United States Patent [19]

Mosbach

[11] 4,021,307

[45] May 3, 1977

[54] METHOD AND APPARATUS FOR MEASURING TEMPERATURE CHANGES GENERATED BY ENZYME ACTIVITY

[75] Inventor: Klaus H. Mosbach, Furulund, Sweden

[73] Assignee: LKB-Produkter AB, Bromma, Sweden

[22] Filed: June 6, 1975

[21] Appl. No.: 584,595

[30] Foreign Application Priority Data

June 7, 1974 Sweden ............................ 7407494

[52] U.S. Cl. .......................... 195/103.5 R; 195/127
[51] Int. Cl.² ...................................... G01N 31/14
[58] Field of Search ............ 195/103.5 R, 127, 115, 195/63; 204/1 E, 195 B; 73/15 R

[56] References Cited

UNITED STATES PATENTS

| 3,542,662 | 11/1970 | Hicks et al. ................ 195/103.5 R |
| 3,847,741 | 11/1974 | Heady et al. ...................... 195/115 |
| 3,878,049 | 4/1975 | Tannenbaum et al. ..... 195/103.5 R |

OTHER PUBLICATIONS

Inman et al., "The Immobilization of Enzymes on Nylon Structures and Their Use in Automated Analysis" Biochem J. (1972), 129, pp. 255–262.

*Primary Examiner*—Alvin E. Tanenholtz
*Assistant Examiner*—C. A. Fan
*Attorney, Agent, or Firm*—George H. Mitchell, Jr.

[57] ABSTRACT

A method and apparatus for measuring temperature changes generated by enzyme activity consists in conducting a matrixbound enzyme through a flowpath formed by a helical coil and sensing the temperature in the immediate vicinity of the flowpath.

7 Claims, 5 Drawing Figures

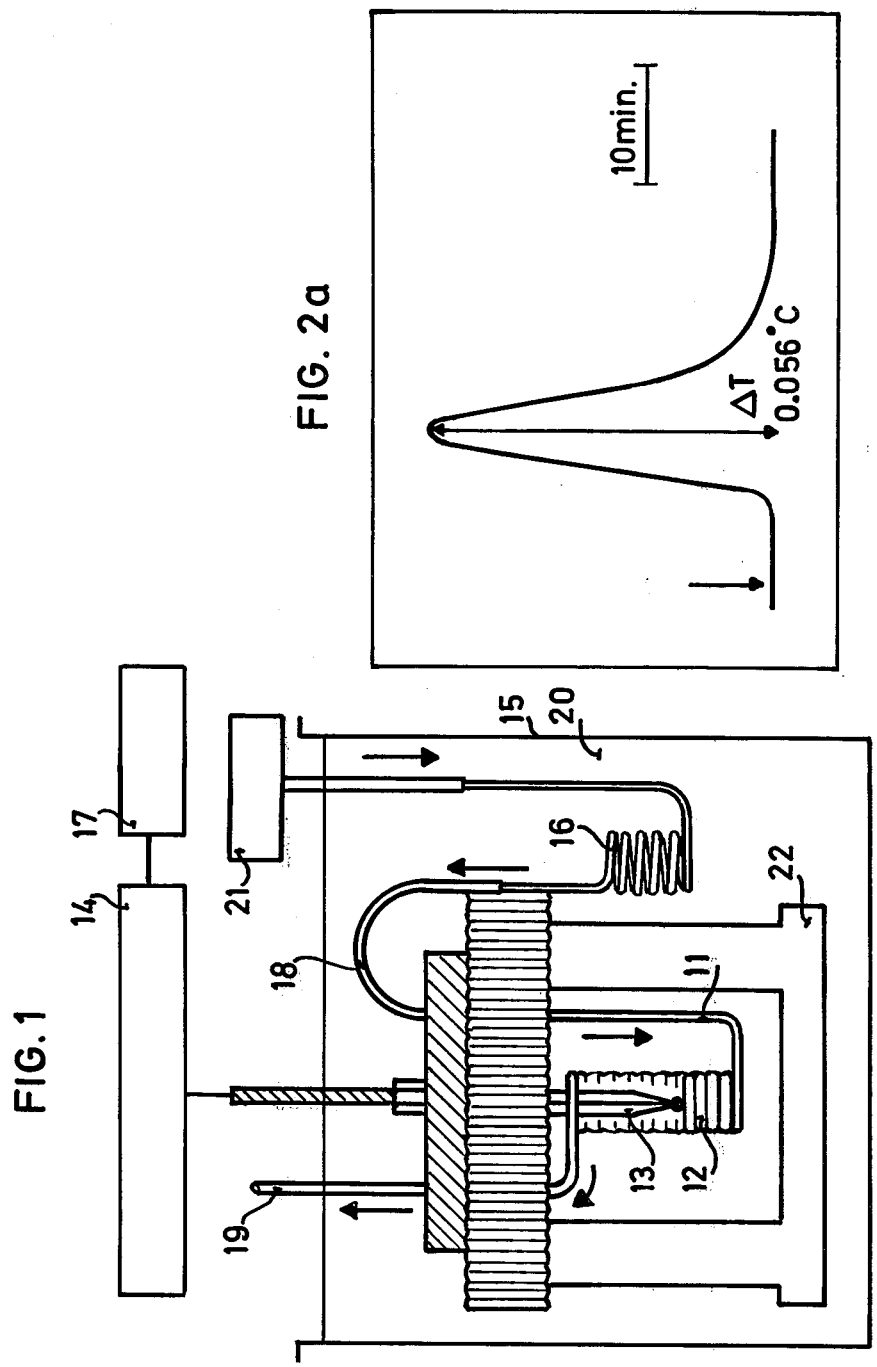

METHOD AND APPARATUS FOR MEASURING TEMPERATURE CHANGES GENERATED BY ENZYME ACTIVITY

The use of microcalorimetry for studying biological systems, enzyme reactions, and especially as a general analytical tool has been subject to a considerable interest during the recent years. Very sensitive and accurate microcalorimeters are now commercially available.

The present invention refers to an alternative method for the thermal analysis of biological systems, comprising enzymes by using a means that could be called an enzyme thermistor. In this case as in an enzyme electrode where the enzyme is located in a liquid film surrounding the electrode or is kept immobilized in a polymerfilm, the sensor is arranged in the immediate vicinity of the location of the reaction. Thus, temperature changes caused by enzyme reactions can easily be measured since these changes are very obvious in the "microenvironment" of proteins.

It has been suggested to immobilize the proteins directly on a heat sensor or thermistor, for example for covering this device by a glutaraldehyde cross linked enzyme or by encapsulating the enzyme in a dialysis bag surrounding the thermistor. Temperature changes can thus be detected although a low rate of efficiency of the enzyme activity or diffusion obstacles for substrate/product through the membrane implies difficulties. Furthermore, high heat losses appear.

According to the present invention it has been shown that a considerably better result is obtained by arranging a heat sensor surrounded by a flow path which comprises matrix-bound enzymes and by passing the substrate which is affected by enzyme activity through the flow-path. The invention refers to a method and an apparatus for measuring temperature changes generated by enzyme activity, the characteristics of the invention appearing from the enclosed claim.

The arranging of the heat sensor directly in a flow-path comprising a bedding of immobilized enzyme has given good results. Thus, it appeared that when the heat sensor was located approximately in the middle of a microcolumn (40 mm × 6 mm) containing about 1 ml packed enzyme carrying glass beads comparable heat responses were obtained by the tested enzymes trypsin, apyrase and urease.

Alternatively, the heat sensor could be located within a flow-path which could be shaped as a helical loop surrounding the sensor. Also in this case good results have been achieved.

The enzymes present in the biological systems can be immobilized on glass or plastic beads, for instance on alkyl amino glass, where the enzyme is linked to the glass via a $-(CH_2)_n-NH_2-$ arm, or can be encapsulated in a porous polyacrylamide.

The invention will be described in detail, reference being made to the enclosed drawings.

FIG. 1 shows schematically a device for carrying out the method of measuring temperature changes according to the invention.

FIGS. 2a, 2b, 3 and 4 show characteristics obtained from experiments carried out in the apparatus shown in FIG. 1.

Figure 2B:
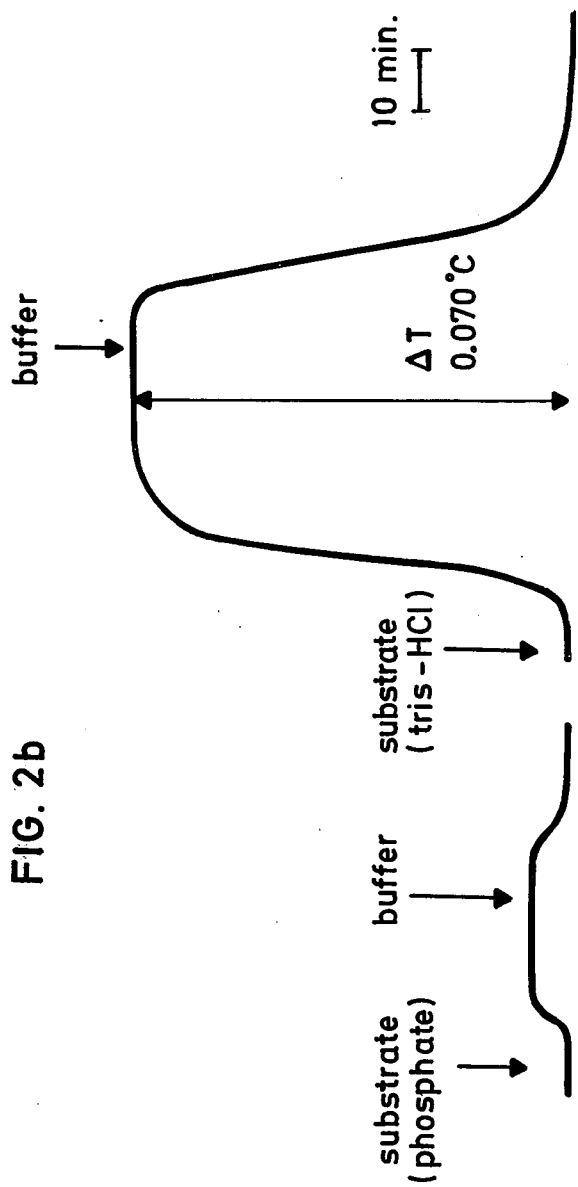

As appears from FIG. 1 the shown apparatus comprises a thermistor 13 (Precision Thermistor YSI No. 44106, Yellow Springs Instrument Co., Ohio, USA with a resistance of 10 $k\Omega$ at 25° Centigrades) as a heat sensor connected to an electronic temperature measuring instrument 14 (Knauer, Wissenschaftlicher Geratebau, W. Berlin). Changes in the resistance of the thermistor caused by temperature variations are measured by this electronic temperature measuring instrument and a modified Wheatstone-bridge equipped with an ultrastable, high sensitive amplifier. Temperature variations are registered directly on a registering recorder 17 (W + W recorder 3001 Kontron, Zurich, Switzerland). The apparatus gives a full scale deflection on the registering recorder (100 mV) at a temperature change ($\Delta T$) of 0.02 degrees centigrades. The thermistor 13 is located within a helical loop 12 made from plastic tubing, suitably polyvinyl tubing (inner diameter 1 mm) which has been glued suitably by means of epoxiresin, and been provided with a bottom so as to form a vessel with an inner diameter of 4 mm. The thermistor runs down into the vessel where it is surrounded by paraffin oil, a liquid known for its low heat capacity, which gives good thermal contact. The loop arrangement is located in an air-filled, double-walled container 22 and thus heat isolated. The container 22 is closed apart from an inlet port 18 and an outlet port 19 connected to the helical loop 12 and a port for introducing the thermistor 13. The complete measuring cell is inserted in a thermostatic bath 20 arranged in a tank 15 (Hetotherm, 0.5 PG 623 UO, Heto Birkerod, Denmark). The inlet port 18 has a part 16 lowered into the bath with a number of loops for regulating the temperature of the incoming fluid and is connected to a pump 21 for the fluid.

In the apparatus described above two enzymes were tested, trypsin and apyrase. It turned out that no reference thermistor was necessary. The loop (total volume 180 $\mu l$) comprised about 100 mg (wet weight) enzyme carrying glass beads and the substrate solution was pumped through the system by means of a peristaltic pump (LKB-Beckman, Perpex) at a low velocity corresponding to 10 ml/h. Matrixbound enzyme preparations are easily pumped into the tubing and are prevented from leaving the tubing by means of a plug made from glass fibres. Buffer and substrate solution was pumped alternatively through the cell by using a threeport valve.

The two tested enzymes, trypsin (Sigma, 2 times crystallized, 36 units/mg) and apyrase (Sigma, potato, quality 1, 1000 U (5'-ATPas-activity)/0.417 gram dry weight; 5'-ATP 2.4 U/mg, 5'-ADP 2.9 U/mg, 5'-AMP 0.05 U/mg) were linked separately to alkylaminoglass beads (diameter 70–150 $\mu$, porous diameter 700 A) after activation by means of 2.5 % glutaraldehyde, according to the procedure developed by Weetall. Trypsin (15 mg) and apyrase (50 mg) were linked to 0.5 gram dry glass beads. The loops carried a total enzymeactivity of about 3 units (trypsin) or 1.5 units (apyrase) based on separate spectrophotometrical determinations.

FIG. 2a shows the response obtained after an injection of a pulse of 1.0 ml 6 mM solution of benzoyl-L-arginine ethyl ester (BAEE) into 0.1 M Tris-HCl, pH 8.0, in the system which contained the glassbound trypsin. For this and all the following measurements such a sensitivity range was chosen that a full scale deflection on the recorder corresponded to a temperature change of 0.1° C.

In FIG. 2b there is shown the response for the same concentration continuously flowing through the system. The fact that the registered temperature change is somewhat higher compared with FIG. 2a depends on the fact that the amount of substrate present in the pulse is not sufficient to give a heat equilibrium as has been discovered by previous use of conventional flow-microcalorimeters. A lower temperature response was obtained when the reaction was carried out in a 0.1 M, pH 8.0 phosphatebuffer instead of a Tris-buffer. It should be emphasized that values on $\Delta H$ for ester hydrolysis reactions usually is close to zero and that the main contribution to the totally registered heat is obtained from a proton-transfer to the buffer from the acid generated. This is in accordance with the values presented in the literature on the generated heat at protonisation of the corresponding Tris- and phosphate buffer system, $\Delta H = -47.48$ kJ/mol and $-4.74$ kJ/mol respectively.

Figure 3:
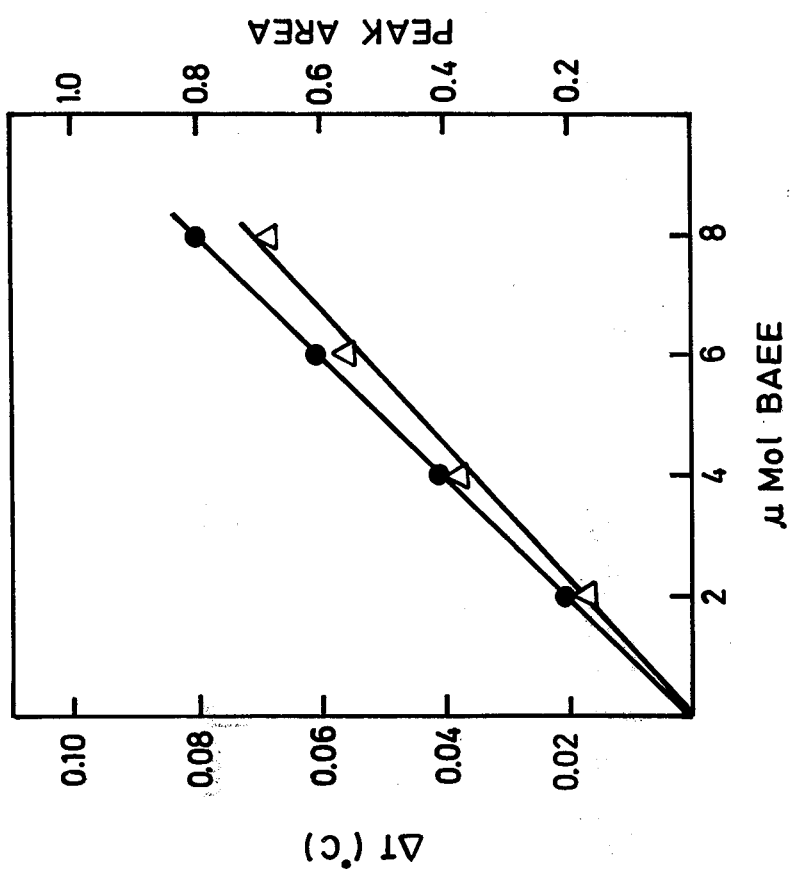

In FIG. 3 the amplitudes of the peaks ($\Delta T$) in °C ($\Delta$-$\Delta$) are presented as a function of the amount of substrate (1 ml solution, 1-8 mM) which is added to an immobilized trypsin. An almost linear relation exists between the registered $\Delta T$ and the amount of substrate added. The response which is obtained after addition of 1 $\mu$mole substrate gives a $\Delta T$ of 0.01° C, corresponding to 10% of full scale deflection ($\Delta T = 0.1$° C) on the diagram of the recorder and could easily and reproducibly be detected. Equivalent relations are obtained when the integrated areas (o-o) under the peaks is compared to the added amount of substrate or when the maximum slope of the curve is introduced. By means of an enzymatic spectrophoto-metrical analysis of the flows it could be shown that by passing the loop containing the glassbound trypsin, the added ester was completely hydrolyzed at all concentrations used. The $\Delta T$ which was obtained from the enzymatic hydrolysis of ATP with glassbound apyrase, was detected as a function of the substrate concentration. The enzyme preparation containing 5'-ATPase, 5'-ADPase and 5'-AMPase (about 1% of the total activity) and thus through the reaction essentially AMP was formed from ATP.

Figure 4:
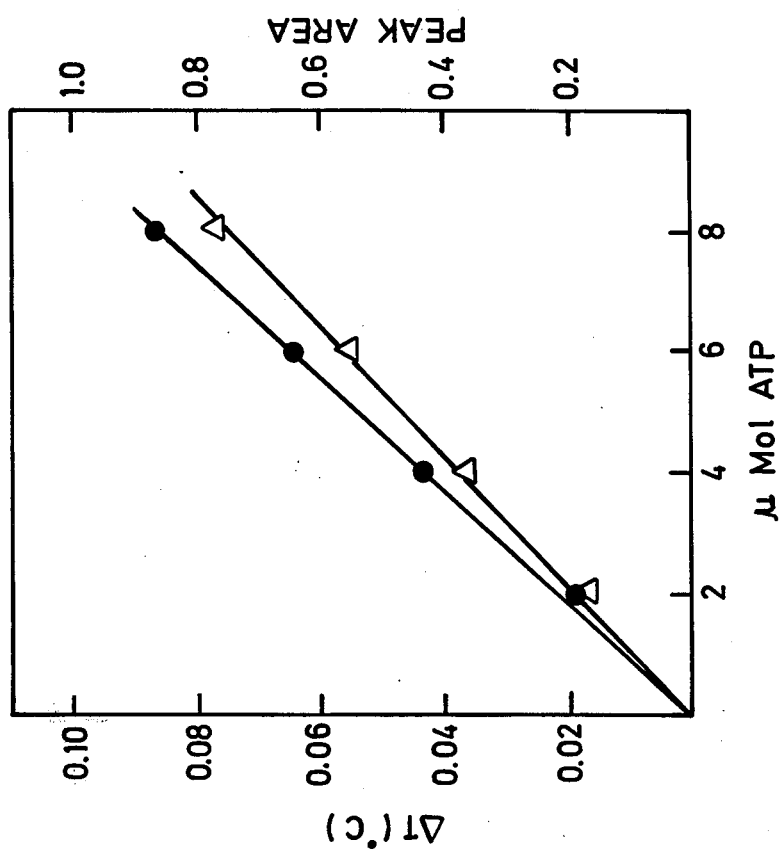

FIG. 4 shows an almost linear relation obtained between the amount of added ATP (1 ml solution, 1-8 mM in 0.1 M Veronal-HC1, 1 mM $CaCl_2$, pH 6.7) and the registered $\Delta T$ i °C ($\Delta$-$\Delta$). As was the case with trypsin, linear relations were also obtained between the amount of added substrate and the integrated area (o-o) of the responses or the maximum slope of the curves. In a control experiment the output flow was analysed after addition of a pulse of 1 ml comprising 8 $\mu$mol ATP on inorganic phosphate. At this ATP-concentration the amount of inorganic phosphate found showed complete hydrolysis of all added ATP to AMP when passing through the loop.

A pulse consisting of 1 ml 10 mM BAEE-solution was supplied to the loop in order to ensure indirectly that the heat generated really is the result of a specific enzyme reaction and is not caused by heat effect derived for instance from substrate diluting. No temperature change was registered. Alternatively, at supply of a pulse of 1 ml 10 mM ATP-solution to the trypsin containing loop only an insignificant temperature response was registered (<5% of the total amount of heat developed with apyrase).

In summary, one could say that the responses measured for both enzyme reactions were big enough to ensure a safe determination of amounts of substrate down to 1 $\mu$mole. The following calculation could be made based on the reported protonisation heat in a tris-buffer. Since a flow of 10 ml/h of 6 mM BAEE generates 800 $\mu$W (0.0167·$10^{-6}$ mol/sec x 47.8 × $10^3$ J) the registered $\Delta T$ of 0.07° C (FIG. 2b) means that a deflection of $\sim$ 0.01° C corresponds to 100 $\mu$W. This could preferably be compared with the sensitivity which is obtained by commercially available advanced flowcalorimeters equipped with specially modified flowcells. By using the principal of arranging the sensor in the immediate vicinity of the reaction sites, the need for special shields or thermopiles which are required in conventional microcalorimeters is eliminated. The above described enzyme thermistor has a number of advantages. One advantage consists in that the matrix bound enzyme preparations which represent a part of the system often are stable and could be used repeatedly. When studying glassbound trypsin, no reduction in the heat response was obtained during long periods of analysis comprising up to 10 days. When the enzyme becomes denatured, it can easily be removed and the loop be filled with new enzyme. The inherent potential of an enzyme thermistor as an analytical tool is obvious, but its use can be extended over several other areas, for instance it could be used as a model system for affinity chromatography. The invention could also be used for clinical analysis, for instance of urea and glucose and has thereby the advantage that fast analysis can be performed. Furthermore the invention can be used when measuring continuous processes and for fermentation processes at the manufacture of penicillin. The enzyme thermistor according to the invention is also cheaper than conventional systems for thermal analysis of biological systems.

Other advantages of the invention consist therein that measurements could be performed in impure solutions, for instance coloured solutions or solutions comprising particles, whereas spectrophotometrical determination methods require pure solutions; a further advantage consisting in that measurements could be performed in connection with a primary enzymatic reaction without the use of further enzymes which is often required in spectrophotometrical determinations; that different substances of a solution could be determined by using different thermistors connected in series by using one and the same volume of substrate solution, thereby only a very small volume of solution being required, which is of interest in medical applications for instance at blood analysis; that the heatsensor according to the invention is a universal sensor and that not only amounts of substrate but also amounts of enzymes could be determined according to the invention which could also be of medical interest.

Examples of enzyme systems in which the invention preferably could be used are penicillinase, urease, glucose oxidase, esterases such as trypsin and apyrase.

I claim:
1. Method for measuring enzyme activities comprising the steps of:
   a. providing a flow path for a fluid, a portion of said flow path being elongated and having a narrow transverse cross-section compared to the length thereof, said elongated portion being confined within a heat-isolated container;
   b. introducing a matrix-bound enzyme preparation into said elongated portion of the flow path;
   c. inserting heat-responsive sensor in intimate heat-exchanging relationship to said matrix-bound enzyme in said elongated flow path;

d. producing a flow of fluid containing a substrate which is affected by said enzyme through said flow path, and;

e. determining the enzyme activity solely by temperature changes sensed by said sensor.

2. The method of claim 1, wherein said elongated portion of the flowpath is arranged to surround said sensor.

3. The method defined in claim 2, wherein said elongated portion of the flowpath is arranged to define a helix.

4. The method of claim 2, which includes the step of conducting said fluid containing a substrate through another portion of said flowpath remote from said sensor and in heat-exchanging relationship to a thermostatic path prior to introducing said fluid containing a substrate to said elongated portion of the flowpath.

5. Apparatus for measuring enzyme activity resulting from contact between matrix-bound enzyme particles and a fluid containing a substrate affected by said enzyme, comprising:

a. a closed container immersed in a thermostatic body of liquid;

b. an elongated conduit defining a flow path for said fluid containing a substrate, a first portion of said flow path being in heat-exchanging relationship to said thermostatic body of fluid, a succeeding portion of the flow path being contained within said closed container in heat-isolating relationship thereto;

c. said succeeding portion of the flow path being elongated and having a narrow cross-section with respect to the length thereof;

d. matrix-bound enzyme particles contained in said succeeding portion of the flow path;

e. heat sensor means in heat-exchanging relationship to said matrix-bound enzyme particles, whereby enzyme activity can be determined solely by temperature changes sensed by said sensor when said substrate flows through said flow path.

6. The invention defined in claim 5 wherein a portion of said conduit surrounds said heat sensor to define said succeeding portion of the fluid flow path.

7. The invention defined in claim 6 wherein said portion of the conduit which surrounds the sensor comprises a tightly wound helix defining the side wall of a vessel, one end of the helix being closed, and a heat-exchanging liquid being contained with said heat sensor in said vessel.

* * * * *